(12) United States Patent
Sarvazyan

(10) Patent No.: US 7,985,184 B2
(45) Date of Patent: Jul. 26, 2011

(54) ULTRASOUND-ASSISTED DRUG-DELIVERY METHOD AND SYSTEM BASED ON TIME REVERSAL ACOUSTICS

(75) Inventor: Armen P. Sarvazyan, Lambertville, NJ (US)

(73) Assignee: Artann Laboratories, Trenton, NJ (US)

( * ) Notice: Subject to any disclaimer, the term of this patent is extended or adjusted under 35 U.S.C. 154(b) by 0 days.

(21) Appl. No.: 12/766,383

(22) Filed: Apr. 23, 2010

(65) Prior Publication Data
US 2010/0204643 A1 Aug. 12, 2010

Related U.S. Application Data

(63) Continuation-in-part of application No. 11/223,259, filed on Sep. 10, 2005, now Pat. No. 7,713,200.

(51) Int. Cl.
*A61B 8/00* (2006.01)
*A61M 5/00* (2006.01)
(52) U.S. Cl. ............... 600/461; 600/464; 604/22
(58) Field of Classification Search .......... 600/447, 600/464, 461, 437; 604/22
See application file for complete search history.

(56) References Cited

U.S. PATENT DOCUMENTS

| 5,092,336 | A | 3/1992 | Fink |
| 6,755,083 | B2* | 6/2004 | Berryman ............... 73/602 |
| 7,089,796 | B2* | 8/2006 | Pepper et al. ............ 73/602 |
| 7,201,749 | B2 | 4/2007 | Govari |
| 7,587,291 | B1* | 9/2009 | Sarvazyan et al. ......... 702/103 |
| 2003/0009153 | A1* | 1/2003 | Brisken et al. ......... 604/890.1 |
| 2004/0030227 | A1* | 2/2004 | Littrup et al. ........... 600/300 |
| 2009/0216128 | A1 | 8/2009 | Sarvazyan |

FOREIGN PATENT DOCUMENTS
EP 1449564 8/2004
* cited by examiner

*Primary Examiner* — Long V Le
*Assistant Examiner* — Helene Bor
(74) *Attorney, Agent, or Firm* — Boris Leschinsky

(57) ABSTRACT

An ultrasound beacon is incorporated into a needle of a drug delivery system utilizing high intensity ultrasound energy during certain cancer treatments. The beacon is configured to generate a electrical feedback signal in response to an initial ultrasound signal sent by an ultrasound transmitter. The electrical feedback signal is then sent along two electrical conductors of the needle and further over a cable back to the electronic unit. The feedback signal is then used to generate high intensity focused ultrasound using time-reversal acoustics principles. Therapeutic application of the system of the invention includes applying high intensity focused ultrasound at the site of drug delivery to enhance local tissue uptake of injected medication.

15 Claims, 6 Drawing Sheets

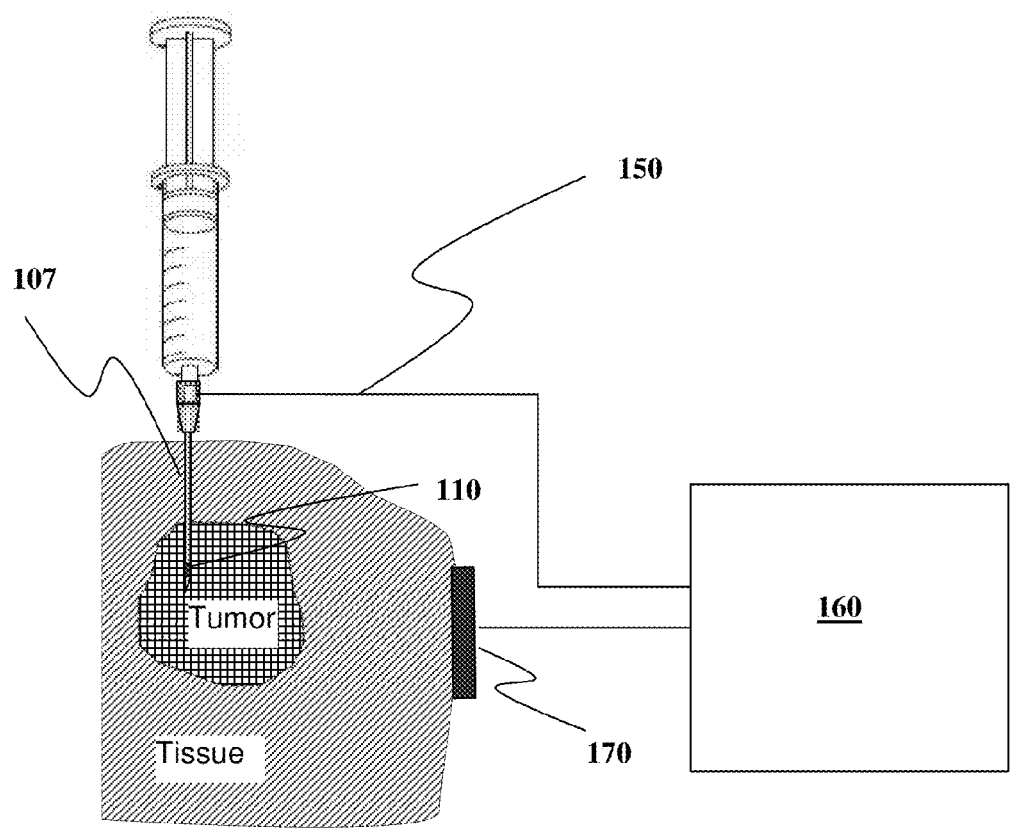
FIGURE 1
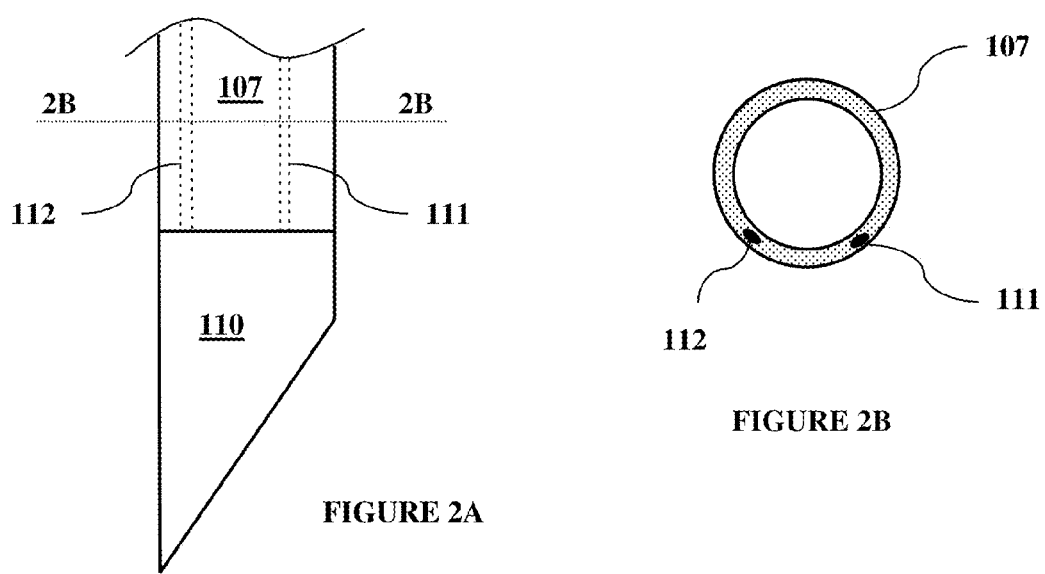
FIGURE 2A
FIGURE 2B

ULTRASOUND-ASSISTED DRUG-DELIVERY METHOD AND SYSTEM BASED ON TIME REVERSAL ACOUSTICS

CROSS-REFERENCE DATA

This application is a continuation-in-part of a U.S. patent application Ser. No. 11/223,259 filed Sep. 10, 2005, now U.S. Pat. No. 7,713,200 entitled "Wireless beacon for time-reversal acoustics, method of use and instrument containing thereof", incorporated herein by reference in its entirety.

REFERENCE TO GOVERNMENT-SPONSORED RESEARCH

This invention was made with the U.S. government support under SBIR grant No. NS065524 entitled "Time-reversal acoustic device for enhanced drug delivery for brain gliomas" and awarded by the National Institute of Health, National Institute of Neurological Disorders and Stroke. The government has certain rights in this invention.

BACKGROUND OF THE INVENTION

The present invention relates to medical devices using Time-Reversal Acoustics (TRA) methods for ultrasound-assisted therapy. One advantageous example of such therapy is needle-based targeted drug delivery into a tumor. Enhanced penetration of drug into the tumor is achieved by subjecting the tumor tissue to ultrasound energy which is focused at the tumor location using the method of the invention. More particularly, a beacon for focusing ultrasound energy is provided at the tip of a dual-function needle, which delivers the drug into the treated tissue and at the same time acts as a hydrophone enabling TRA system to focus ultrasound exactly at the site where the drug was injected.

Focusing of ultrasonic waves is a fundamental aspect of most medical applications of ultrasound. The efficiency of ultrasound focusing in biological tissues is often significantly limited by spatial heterogeneities in sound velocity in tissues and the presence of various reflective surfaces and boundaries. The refraction, reflection and scattering of ultrasound in inhomogeneous media can greatly distort focused ultrasound field. There are many methods for improving the ultrasonic focusing in complex media based on the phase and amplitude corrections in focusing system but they are often too complicated and in some cases do not provide necessary improvement. The concept of TRA developed initially by M. Fink of the University of Paris provides an elegant possibility of both temporal and spatial concentrating of acoustic energy in highly inhomogeneous media. The TRA technique is based on the reciprocity of acoustic propagation, which implies that the time-reversed version of an incident pressure field naturally refocuses on its source. The general concept of TRA is described in an article by Fink, entitled "Time-reversed acoustics," Scientific American, November 1999, pp. 91-97, which is incorporated herein by reference. U.S. Pat. No. 5,092,336 to Fink, which is also incorporated herein by reference, describes a device for localization and focusing of acoustic waves in tissues.

An important issue in the TRA method of focusing acoustic energy is related to obtaining initial signal from the target area. It is necessary to have a beacon to provide an initial signal from the focal region. In the TRA systems described in the prior art, most common beacon is a hydrophone placed at the chosen target point. Other possible beacons are highly reflective targets that provide an acoustical feedback signal for TRA focusing of acoustic beam.

Remarkably, scattering and numerous reflections from boundaries, which may greatly limit and even completely diminish conventional focusing, lead to the improvement of the focusing ability of the TRA system. Fink et al. have demonstrated a strong robustness of TRA focusing: the more complex the medium, the sharper the focus.

The advantages of the TRA-based focusing systems (TRA FS) over conventional ultrasound focusing are as follows:

1. TRA FS is capable to precisely deliver ultrasound energy to the chosen region regardless of the heterogeneity of the propagation medium, for example behind the ribs or inside the skull. The ability to effectively localize ultrasound energy and avoid exposure of surrounding tissues is important in many medical applications including ultrasound surgery and the ultrasound enhanced drug delivery.
2. TRA FS can produce more effective spatial concentration of ultrasound energy than traditional systems; the focus volume can approach ultrasound diffraction limit, it can be spherical rather than elongated ellipsoidal typically formed by most traditional focusing systems.
3. TRA FS can produce pulses with arbitrary waveforms in a wide frequency band. Ability to generate various waveforms is important in many applications, for example for optimizing the outcome of the ultrasound stimulated drug delivery where the main mechanism of ultrasound action, sonoporation, is related to cavitation and the threshold of cavitation depends strongly on frequency and the form of the applied signal.

Several examples of TRA FS employing a passive ultrasound reflector or an active ultrasound emitter as a TRA beacon are described in the U.S. Pat. No. 7,201,749 to Govari et al. as well as a European Patent Application No. EP1449564, all of which are incorporated herein by reference. Described is a TRA-based high intensity ultrasound system designed for isolation of pulmonary veins. The beacons, described in these references, are active or passive piesotransducers designed to reflect or emit ultrasound signal to be detected by an array of transducers. In case of an active beacon, the electrical energy is typically delivered thereto via electrical leads from the control unit. The electrical energy is converted by the active beacon into the acoustic energy and transmitted to the outside the body where it is picked up by outside sensors to determine the exact location of the beacon. Alternatively, the beacon may comprise a passive ultrasound reflector, such as the one having a geometry that produces a sharp and easily distinguishable ultrasound signature. Alternative designs of the reflector include the design with substantially higher reflectivity of the ultrasound signal then that of the surrounding tissues, including the design of the beacon with predefined resonant frequency and high Q or a bubble containing an ultrasound agent.

An important area of medical application of ultrasound is targeted drug delivery, specifically for cancer treatment. Tumor chemotherapy is often associated with severe side effects caused by the interactions of cytotoxic drugs with healthy tissues. In addition, tumor cells often develop resistance to drugs in the course of chemotherapy (cross-resistance or multi-drug resistance). Direct injection of drugs in the tumor substantially reduces or eliminates side effects of chemotherapy and increases therapeutic windows of drugs.

Acoustically-activated drug delivery systems are typically therapeutic agents bound to nano- or micro-scale carriers. These are administered to a patient and then activated by extracorporeal ultrasound transducers. Acoustic activation releases the therapeutic agent and induces cavitation that enhances drug uptake in the patient's cells. A high dosage of toxic drugs may be delivered to a point of interest while minimizing negative side effects.

Acoustic activation technology shows promise for the treatment of drug-resistant cancer tumors and other diseases. Triggering the intracellular drug uptake by focused ultrasound enhances treatment efficacy. Ultrasound is proven to be an effective drug delivery modality. An advantage of ultrasound in this application is that it is non-invasive, can penetrate deep in the interior of the body, and can be carefully controlled via a number of parameters including frequency, power density, duty cycle, and time of application. Physicians do not currently have a means to accurately sonicate only an area of interest where the drug has been injected, in order to improve drug uptake to diseased cells and reduce side effects to healthy tissue.

SUMMARY OF THE INVENTION

Accordingly, it is an object of the present invention to overcome these and other drawbacks of the prior art by providing a method and a dual-function needle which delivers the drug in the target tissue and includes a beacon at its tip configured to provide TRA feedback signal from the site in the tissue where a drug was injected to the TRA electronic unit.

The system of the invention includes a dual-function needle with a piezoelectric beacon incorporated in its tip or at the end of a stylet configured to fit inside the needle. Various designs are disclosed including using the metal body of the needle as one of two electrical conductors for operating the beacon. Once the needle is placed at the target tissue (which may be optionally assisted with ultrasound or other image guidance), the beacon is used in focusing of ultrasound signal on the tip of the needle. Initial ultrasound signal is sent by an external transmitter. It is received by the beacon and converted to an electrical feedback signal which is then sent back to the electronic unit where a focused ultrasound signal is created using TRA principles. The drug is injected before or in some cases after the focusing process and the focused ultrasound system is activated to facilitate better uptake of the injected drug by the surrounding tissue.

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 1 is a general schematic depiction of the system of the invention when used for local drug delivery including the needle according to the first embodiment of the invention, FIGS. 2A and 2B are a side view of the needle and a cross-section thereof according to the second embodiment of the invention.

DETAILED DESCRIPTION OF THE PREFERRED EMBODIMENTS OF THE INVENTION

Figure 3A:
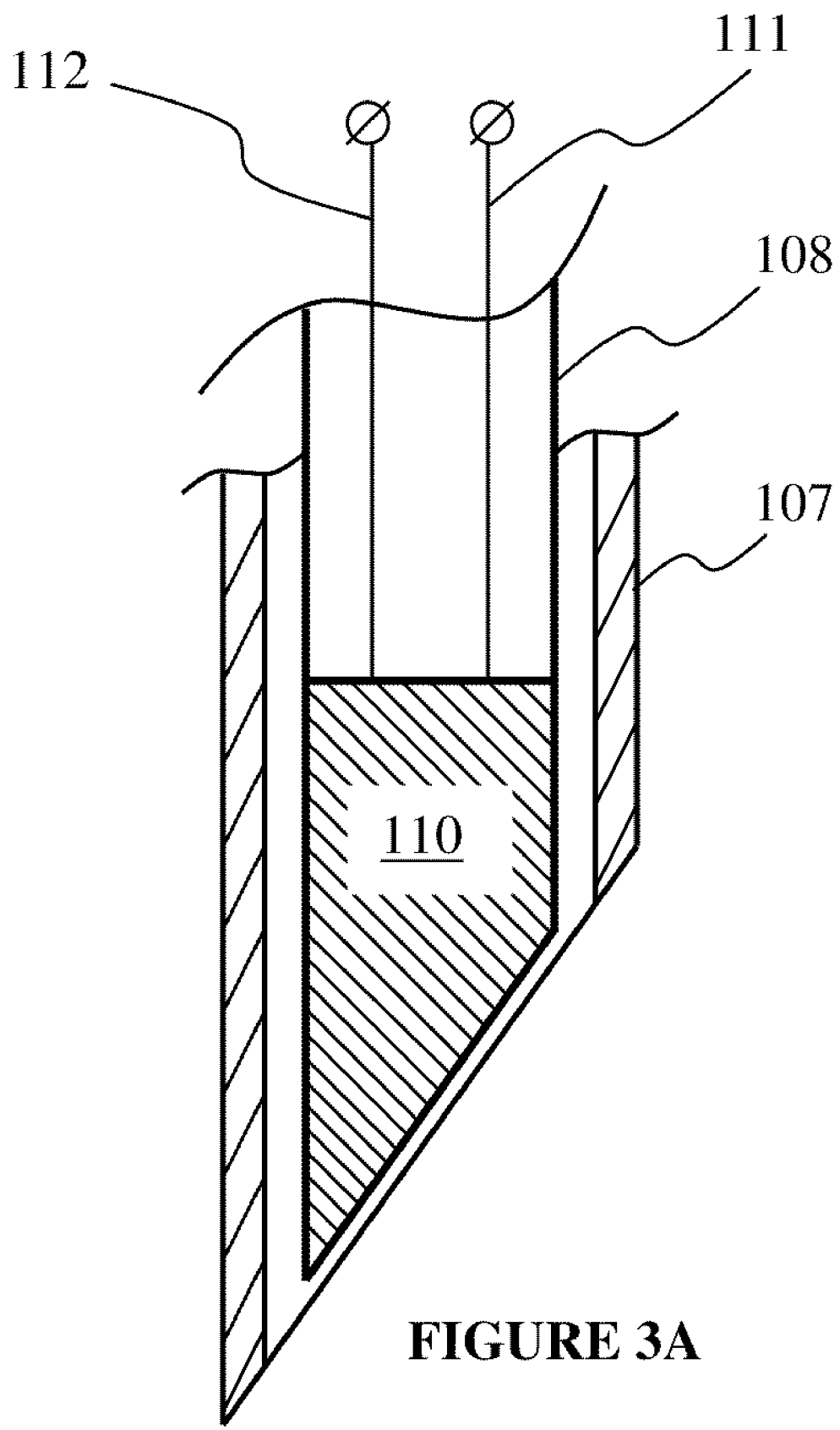
FIGS. 3A and 3B are cross-sections of the needle with various types of a stylet according to the third embodiment of the invention.

A detailed description of the present invention follows with reference to accompanying drawings in which like elements are indicated by like reference letters and numerals.

FIG. 1 depicts a general view of an ultrasound-assisted drug delivery system based on TRA focusing of ultrasound energy to the target tissue. This system may be especially useful in treating cancer tumors. Generally speaking, chemotherapy agents target the cancerous cells by attacking cells that undergo frequent cell division. Active cell growth is a common criteria used to differentiate tumor cells from normal cells. Because some normal cells in the body undergo physiologically-normal cell growth, such as blood cells and cells in the bone marrow, many cancer drugs must be limited in dose to prevent lethal toxicity arising from damaging growth restriction to these healthy cells. Therefore, needle injection of the chemotherapeutic agent directly to the tumor site remains an attractive solution. Ultrasound enhancement of the drug uptake by cancer cells are desired to achieve the best possible outcome.

According to the invention, a dual-function needle ("smart needle") with a beacon in a form of a piezoelectric element embedded at its tip is used to both deliver the drug into the tumor and to enhance intracellular uptake of the injected drug. The piezoelectric element at the tip of "smart needle" acts as a beacon for the Time Reversal Acoustic (TRA) focusing of high intensity ultrasound in the selected site of the tissue to preferentially release the drug.

FIG. 1 depicts the integrated ultrasonic system for drug delivery for cancer treatment comprising a needle 107 with a beacon 110 located at its tip. The beacon may be made using a piezopolymer film serving as a piezoelectric element generating an electrical feedback signal when activated by an initial ultrasound signal. Alternatively, the beacon may be made of a piezoceramic tube or other piezomaterial. The initial ultrasound signal is sent by a transmitter 170 energized by the electronic unit 160. The transmitter 170 typically consists of one or several transducers attached to a reverberator. The electrical feedback signal is then transmitted from the piezoelectric element 110 by electrical conductors along the needle 107 and carried out using a cable 150 back to the electronic unit 160. TRA transformation is conducted by the unit 160 and the transmitter 170 is then energized to generate high intensity ultrasound focused at the location of the beacon 110 and therefore at the drug injection site in the tissue. The details of generating an initial ultrasound signal and subsequent TRA transformation are described in U.S. patent application Ser. No. 12/036,531 and U.S. Pat. No. 7,587,291, both incorporated herein by reference in their entirety. The needle may be optionally guided towards the appropriate location within the tissue using ultrasound imaging means (not shown in FIG. 1) as described below in more detail.

In use, a physician directs the "smart needle" 107 to the target site. Once the needle is positioned at the selected site within the tumor, the drug is injected. After that, the electronic unit 160 causes the transmitter 170 to send an initial ultrasound signal. This signal is received by the beacon 110 and transformed into an electronic feedback signal. The electronic unit 160 receives this feedback signal and uses it to generate a high intensity focused ultrasound with required spatial, temporal and energy parameters for enhancing the therapeutic efficacy of the injected drug.

According to one method of the invention, the needle remains at the tumor site throughout the processes of drug injection and generating high intensity focused ultrasound. Having the needle with the beacon continuously present at the site of injection allows periodic adjustment of the ultrasound field by repeating the focusing procedure. This method is advantageous in the case of extended ultrasound treatment time when the tumor tissues may shift during the procedure and affect the focusing of ultrasound at the site of drug delivery.

In another method of the invention, once the focusing step is complete, the needle is withdrawn and the high intensity focused ultrasound is provided using just the initial focusing procedure. This method may be employed in cases when no significant tissue shift is anticipated throughout the procedure.

According to the first embodiment of the invention, the "smart needle" 107 includes a piezoelectric element 110 mounted on its distal tip. The piezoelectric element generates an electrical signal in response to the received acoustic signal and therefore it is connected to two electrical conductors configured to send the signal back towards the electronic unit 160. According to this embodiment, an insulated microwire and the metal needle body will serve as a first and a second (ground) conductor respectively. The piezoelectric element may be preferably made from polyvinylidene fluoride (PVDF) piezopolymer film. This material is commercially available and widely used in hydrophones and in other applications. A conventional needle may be modified to include a piezopolymer film and a microwire attached along its side. In other embodiments, the microwire may be placed into a shallow grove made along a side of the needle. Once both the piezoelectric element and the microwire are in place, the needle can be subjected to a surface treatment or thin film deposition to encapsulate beacon components and enhance its biocompatibility, corrosion resistance, chemical compatibility, microbial resistance, etc. Teflon coating is preferably applied, but other suitable treatments such as polymer vapor deposition or plasma treatment can also be used.

According to a second embodiment of the invention shown in FIGS. 2A and 2B, the "smart needle" 107 has a cylindrical body made from a hard non-conductive polymer such as for example polypropylene. The body of the needle includes two electrical conductors 111 and 112 imbedded therein and connected to a piezoelectric element 110 imbedded at the tip of the needle. The internal cross-sectional shape of the needle is shown as round in the drawings but it may be of any other appropriate shape to accommodate the conductors 111 and 112. Conductors themselves may be made using a wire of round, oval, or rectangular cross-section such as a ribbon wire.

A third embodiment of the invention includes providing a needle made from a soft non-conductive material with the beacon incorporated at its tip and including two electrical conductors as described above. During the initial insertion of the needle, a hard stylet is placed inside the needle making it rigid. Once at the site, the stylet is removed and the needle remains in the tissue. The drug is then infused gradually from the open end of the needle. The focusing of ultrasound field is conducted initially and then on a periodic basic throughout the procedure of drug infusion. This embodiment is beneficial in situations where infusion of drug and uptake thereof by the tissue will take considerable time. Making the needle from a soft material will increase safety of the procedure since any inadvertent movement of the needle hub after its initial insertion will be less likely to transmit to its tip.

An alternate version of this embodiment is shown in FIG. 3A and includes the piezoelectric element 110 (the beacon) with its two electrical conductors 111 and 112 incorporated within the internal removable stylet 108 and a standard hollow needle 107. The tip of the stylet is configured to be flush with the angled tip of the needle when the stylet is placed in the needle. The beacon is then used to conduct electrical feedback signal from the incoming initial ultrasound signal back to the electronic unit 160. Once the focusing procedure is complete, the stylet 108 is removed and the drug is injected. High intensity focused ultrasound is then delivered to the site where the drug was injected. The advantage of this embodiment is the ability to use the invention with any commonly used hollow needle.

Figure 3B:
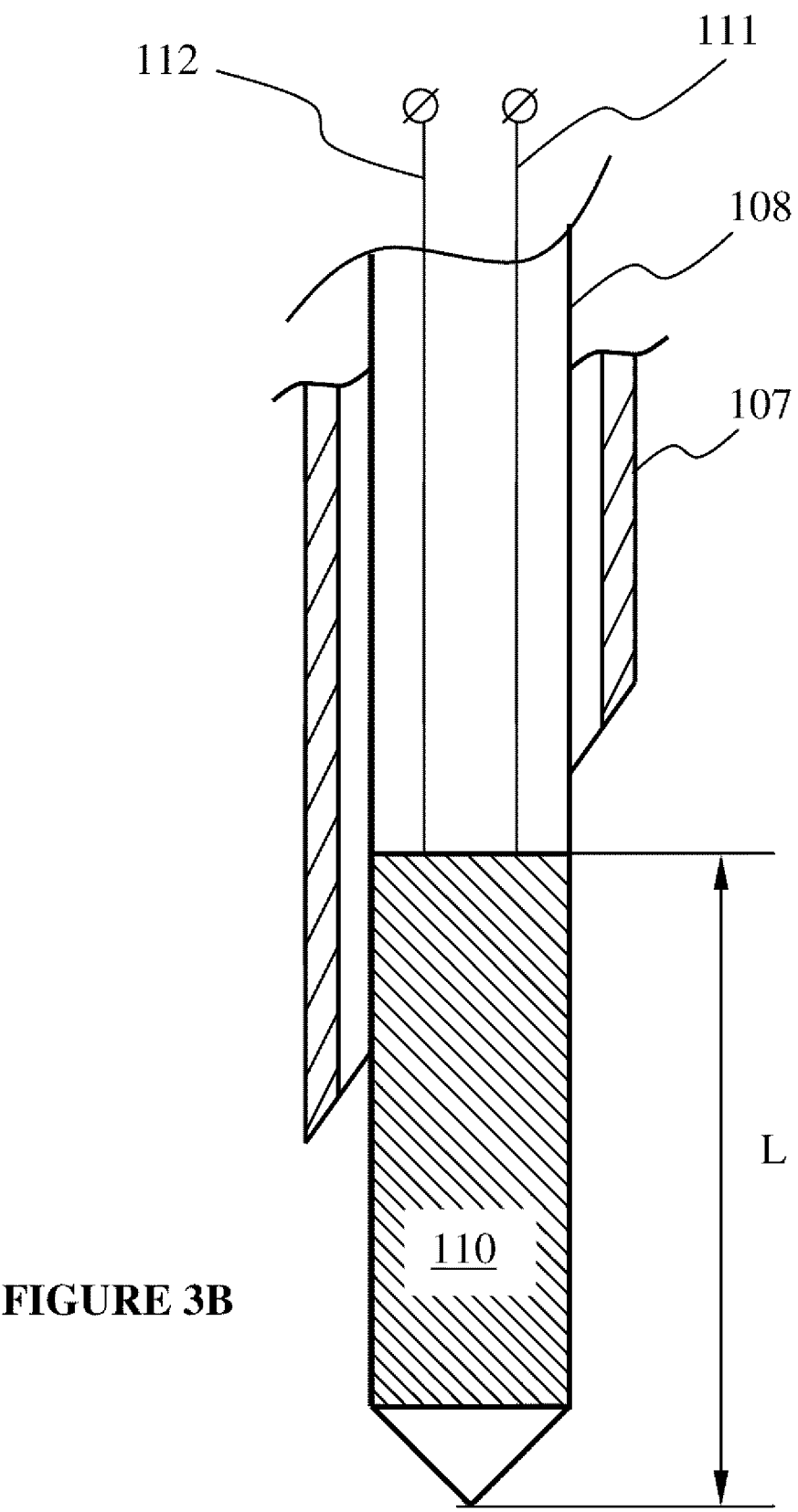

FIG. 3B shows an alternative version of the third embodiment of the invention in which the stylet is configured to protrude through the needle tip by a distance L so as to place the beacon 110 distally from the opening of the needle. When high intensity ultrasound is focused on the beacon, the center of the ultrasound focal spot will more accurately correspond to the center of the zone where the injected drug is located. The distance L may be selected to be equal to one wavelength of the ultrasound wave because TRA focusing of ultrasound typically provides a focal spot with a diameter of about one such wavelength. The ultrasound wavelength depends on the ultrasound frequency. For a typical frequency of 1 MHz, the ultrasound wavelength is approximately 1.5 mm and so the length L is about 1.5 mm. For higher frequencies, the length L will be reduced accordingly and for lower frequencies it will be respectively increased. In use, the hollow needle is first inserted and the tip is located at the target tumor site. The drug is then injected and the stylet is inserted. Once focusing of ultrasound is achieved, the stylet and the needle may be optionally removed and high-intensity ultrasound is then generated.

Figure 4:
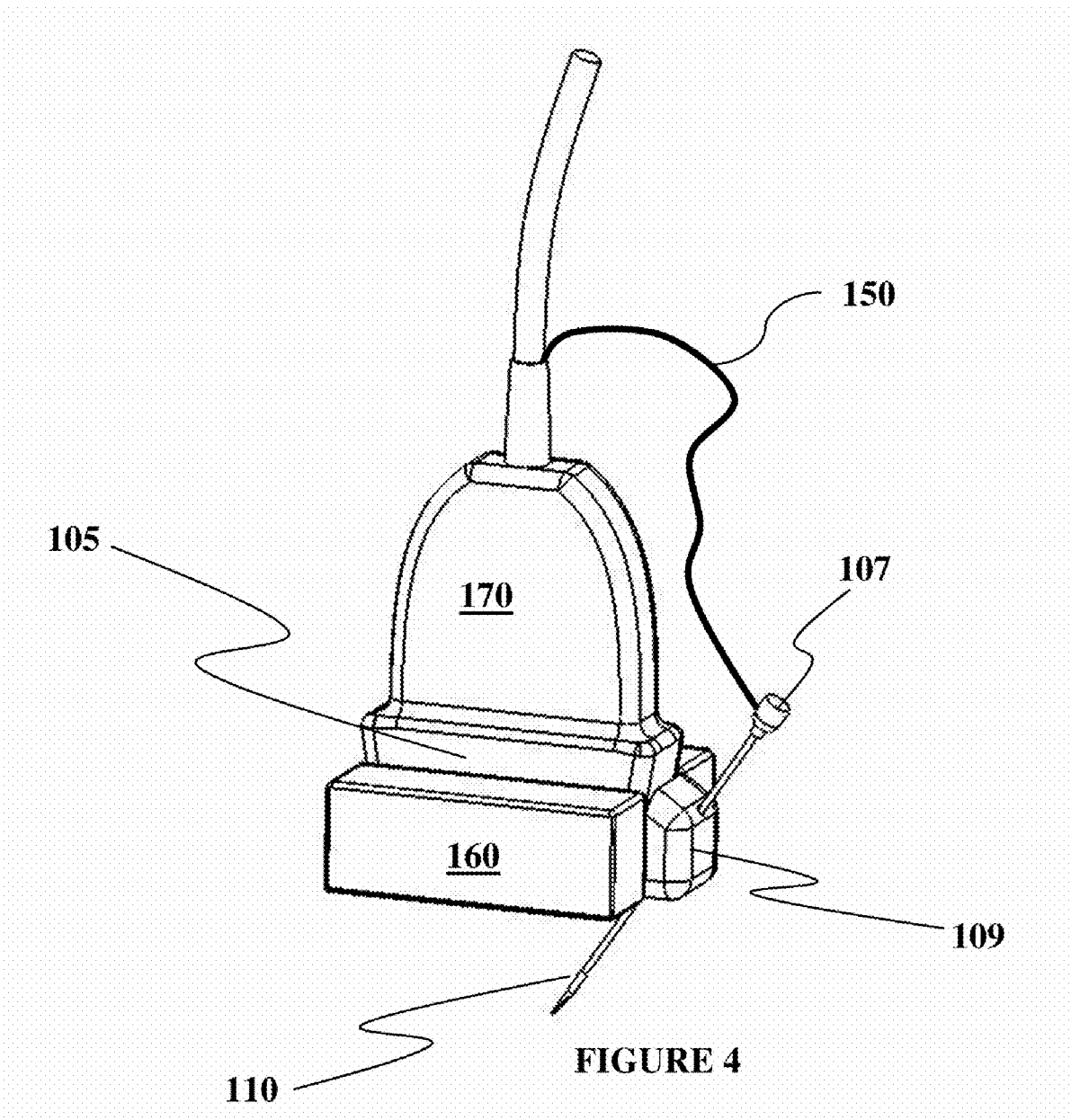
FIG. 4 is the general view of a combined ultrasound probe with TRA reverberators attached along the sides of imaging array shown here with an optional needle guide.
Figure 5:
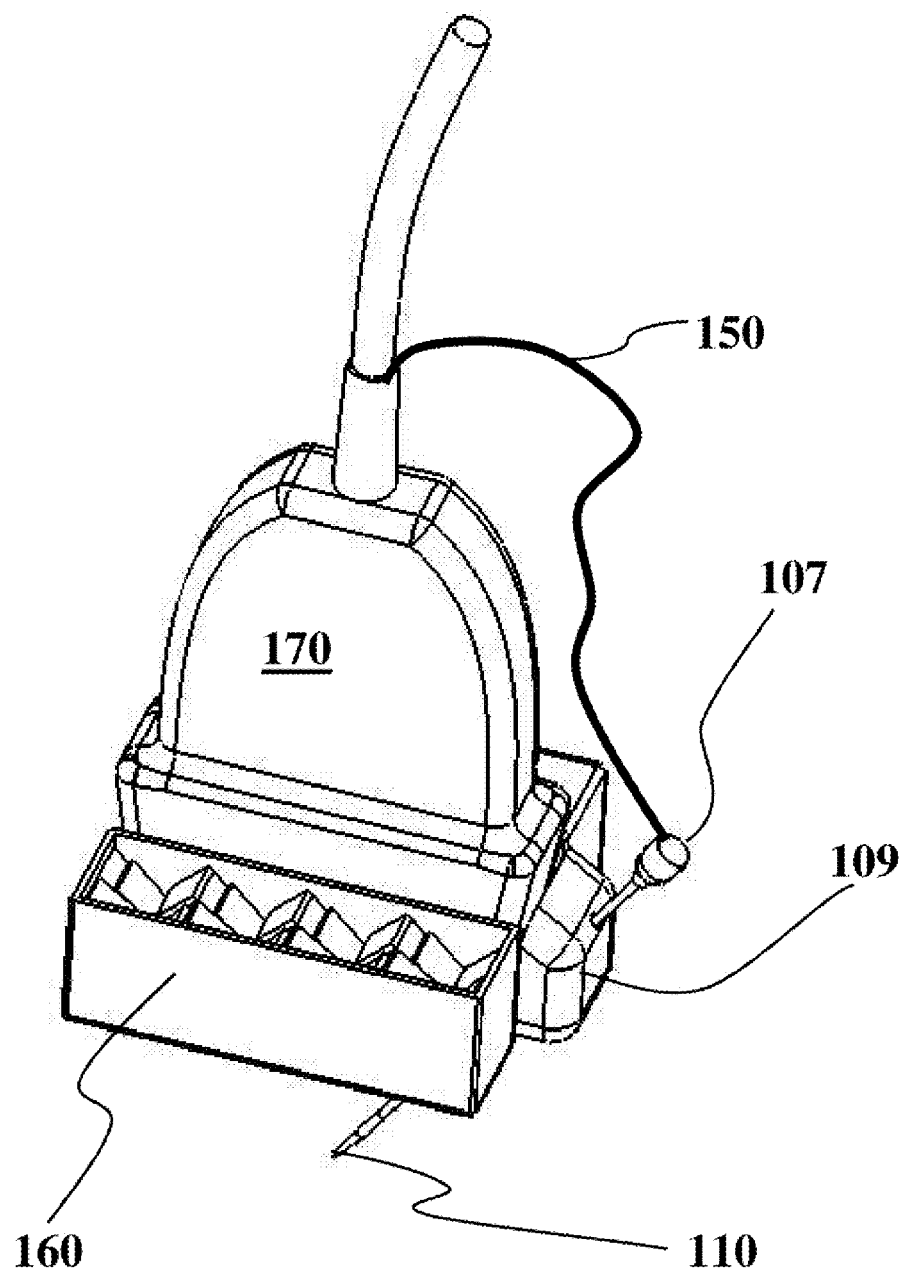
FIG. 5 is the top view of the device shown on FIG. 4 showing the details of TRA reverberators.
Figure 6:
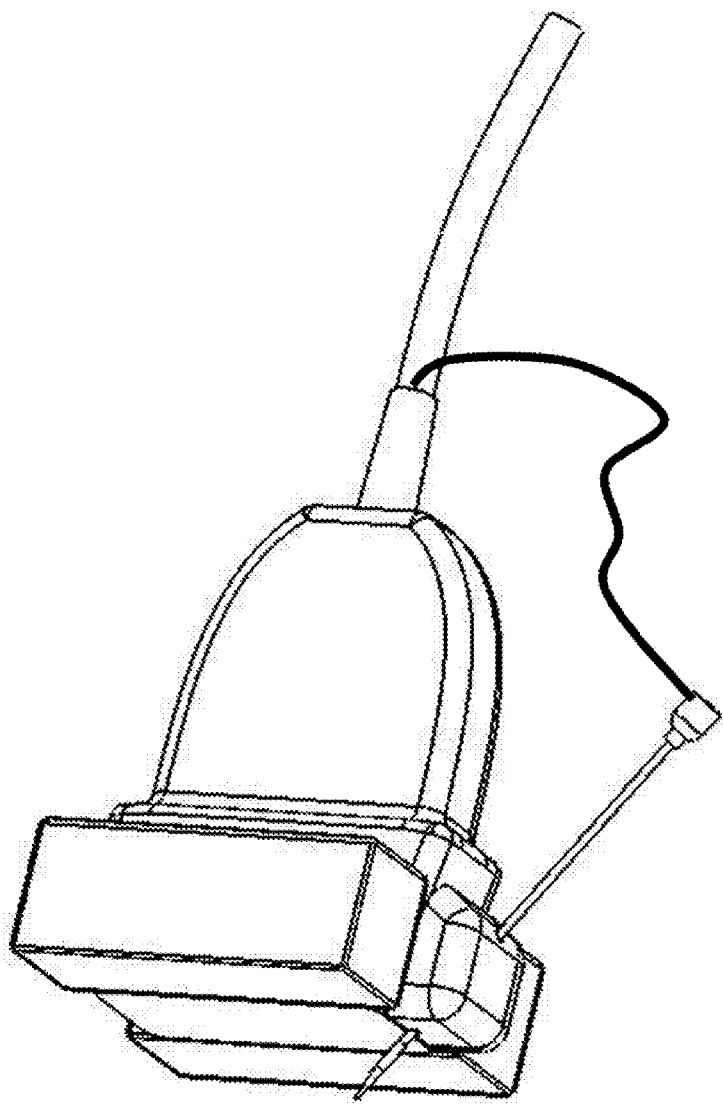
FIG. 6 is the bottom view of the device shown on FIG. 4.

FIGS. 4-6 show the details of an image-guided apparatus used with the "smart needle" of the invention. Shown in these drawings is a generic ultrasound probe combined with TRA reverberators attached along the sides of the imaging array of the probe. An optional needle guide may also be used with this device. An acoustic system shown on the drawings is capable of TRA-based ultrasound-assisted drug delivery. The ultrasound imaging probe 170 is combined with TRA transmitter 160 containing a pair of reverberators on both sides of the probe 105. Each reverberator has a multifaceted design with a plurality of transducers attached to individual facets of the reverberator. These transducers are individually connected with the output channels of the TRA focusing system. Each transmitter is energized via appropriate electrical cables not shown in the drawings. In use, each transmitter may be focused separately using its own initial ultrasound signal. Once all transducers have been focused and individualized TRA-derived ultrasound signals have been generated for all of them, the combined high-intensity ultrasound can be generated by activating all transducers at the same time.

A cable 150 is provided for connection with needle 107. Since the beacon 110 will always be at the tip of the needle 107, incorporating a short cable 150 with the probe 110 is an appropriate solution. An optional needle guide 109 is used for positioning the needle 107 during insertion.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A method for ultrasound-assisted drug delivery, said method including the steps of:
   (a) providing a dual-purpose needle with a tip equipped with a beacon, said beacon including a piezoelectric element connected to a cable via two electrical conductors,
   (b) providing a time-reversal acoustic system including an electronic unit and an external ultrasound transmitter, said cable connecting said needle to said electronic unit,
   (c) inserting said needle to position the tip thereof at the target tissue,
   (d) injecting a drug into said tissue through said needle,
   (e) generating an initial ultrasound signal by said external transmitter,
   (f) receiving said initial ultrasound signal by said beacon and generating an electrical feedback signal,
   (g) sending said signal along said needle via said two electrical conductors to said cable and further to said electronic unit, and
   (h) focusing high intensity ultrasound at a location of said beacon by a time-reversing procedure using said electrical feedback signal.

2. The method as in claim 1, wherein said step (d) is conducted after completion of said step (g).

3. The method as in claim 1, wherein said steps (e) through (g) are repeated on a periodic basis throughout the procedure of drug delivery to refocus said high intensity acoustic energy at a location of said beacon.

4. An ultrasound-assisted drug delivery system comprising:
   a dual-purpose needle having a hollow metal body and a tip equipped with a beacon formed by a piezoelectric element connected to a cable by an insulated microwire running along said needle as a first electrical conductor and by said metal body as a second electrical conductor, and
   a time-reversal acoustic system including an electronic unit and an external ultrasound transmitter, said cable connecting said needle to said electronic unit,
   wherein said electronic unit is configured to first cause said external transmitter to send an initial ultrasound signal, said piezoelectric element receiving said initial signal and generating an electrical feedback signal to be sent along said needle back to said electronic unit via said cable, said electronic unit further configured to focus high intensity ultrasound at a location of the beacon of said needle by a time-reversing procedure using said electrical feedback signal.

5. The system as in claim 4, further including an ultrasound image-guiding means configured for guiding said needle during insertion thereof.

6. The system as in claim 4, wherein said piezoelectric element is a strip of piezopolymer film mounted on said tip of said needle.

7. The system as in claim 4, wherein said piezoelectric element is a piezoceramic tube mounted on said tip of said needle.

8. The system as in claim 4, wherein said needle has a metal body and said piezoelectric element is connected to an insulated microwire as a first conductor and said metal body as a second conductor.

9. The system as in claim 4, wherein said external ultrasound transmitter comprises a reverberator with at least one ultrasound transducer attached thereto.

10. The system as in claim 9, wherein said external ultrasound transmitter comprises a plurality of transducers attached to said reverberator, each transducer attached to a dedicated output channel of a TRA focusing system of said electronic unit, said electronic unit further configured to conduct focusing procedure individually for each transducer and then generate high intensity focused ultrasound by activating all transducers at the same time.

11. An ultrasound-assisted drug delivery system comprising:
    a dual-purpose needle having a hollow non-conductive body and a tip equipped with a beacon including a piezoelectric element connected to a cable by two electrical conductors imbedded into said non-conductive body of said needle, and
    a time-reversal acoustic system including an electronic unit and an external ultrasound transmitter, said cable connecting said needle to said electronic unit,
    wherein said electronic unit is configured to first cause said external transmitter to send an initial ultrasound signal, said piezoelectric element configured to generate an electrical feedback signal in response to said initial signal and to send said electrical feedback signal along said needle back to said electronic unit via said cable, said electronic unit further configured to focus high intensity ultrasound at a location of the beacon of said needle with a time-reversing procedure using said electrical feedback signal.

12. The system as in claim 11, wherein said needle is made from a hard non-conductive polymer material.

13. The system as in claim 11, wherein said needle is made from a soft non-conductive material, said needle further including a rigid removable stylet adapted to make said needle rigid during insertion.

14. An ultrasound-assisted drug delivery system comprising:
    a dual-purpose needle having a removable stylet equipped with a beacon at a tip thereof, said beacon including a piezoelectric element connected to a cable by two electrical conductors contained within said stylet, said cable connecting said stylet to said electronic unit, and
    a time-reversal acoustic system including an electronic unit and an external ultrasound transmitter,
    wherein said electronic unit is configured to first cause said external transmitter to send an initial ultrasound signal, said piezoelectric element configured to generate an electrical feedback signal in response thereto and send it along said needle back to said electronic unit via said cable, said electronic unit further configured to focus high intensity acoustic energy at a location of the beacon of said stylet with a time-reversing procedure using said electrical feedback signal.

15. The system as in claim 10, wherein said stylet protrudes through said tip of said needle such that said piezoelectric element is spaced out from the tip of said needle by a distance equal to about one wavelength of said ultrasound.

* * * * *